United States Patent

Ansmann et al.

[11] Patent Number: 5,686,087
[45] Date of Patent: Nov. 11, 1997

[54] COSMETIC AND/OR PHARMACEUTICAL FORMULATIONS WITH AN IMPROVED FEELING ON THE SKIN BASED ON MIXED GUERBET ALCOHOLS

[76] Inventors: Achim Ansmann, Kirchberg 25, 40699 Erkrath; Rolf Kawa, Fontanestr. 18, 40789 Monheim; Klaus-Michael Mohr, Gustaf-Freytag-Str. 10, 42327 Wuppertal; Josef Koester, Faehrstr. 226, 40221 Duesseldorf, all of Germany

[21] Appl. No.: 663,035

[22] PCT Filed: Nov. 30, 1994

[86] PCT No.: PCT/EP94/03974

§ 371 Date: Jun. 10, 1996

§ 102(e) Date: Jun. 10, 1996

[87] PCT Pub. No.: WO95/15743

PCT Pub. Date: Jun. 15, 1995

[30] Foreign Application Priority Data

Dec. 8, 1993 [DE] Germany ............... 43 41 794.9

[51] Int. Cl.$^6$ .............. A61K 7/48; A61K 47/10; A61K 47/14
[52] U.S. Cl. .............. 424/401; 514/785; 514/786
[58] Field of Search .............. 424/401; 514/785, 514/786

[56] References Cited

FOREIGN PATENT DOCUMENTS

| 0453603 | 10/1991 | European Pat. Off. . |
| 0617952 | 10/1994 | European Pat. Off. . |
| 9317968 | 2/1994 | Germany . |
| 780801 | 8/1957 | United Kingdom . |
| WO9207543 | 5/1992 | WIPO . |

OTHER PUBLICATIONS

Seifen–Öle–Fette–Wachse, vol. 117, No. 10, 1991 Augsburg, De, pp 369–371, Ansmann et al. 'Cosmetic Water in Oil Emulsions– How to Formulate Elegant Skin Care Products'.

Fette, Seifen, Anstrichmitt. 87, p. 403 (1985).

A. Ansmann, SOFW–Journal, 120, 158 (1994).

Soap Cosm. Chem. Spec. Apr., 52 (1987).

"Kosmetische Färbemittel" of the Farbstoffkomission der Deutschen Forschungsgemeinschaft, published by Verlag Chemie, Weinheim, 1984, pp. 81 to 106.

*Primary Examiner*—Frederick Krass
*Attorney, Agent, or Firm*—Ernest G. Szoke; Wayne C. Jaeschke; Real J. Grandmaison

[57] ABSTRACT

A cosmetic or pharmaceutical composition having an improved feel on the skin containing Guerbet alcohols based on fatty alcohol mixtures containing 6 to 12 carbon atoms or esters thereof with fatty acids containing 6 to 22 carbon atoms as oil components, wherein the spreading value of the oil components as determined by the Zeidler method is from about 300 to about 1,000 mm$^2$/10 minutes.

3 Claims, No Drawings

COSMETIC AND/OR PHARMACEUTICAL FORMULATIONS WITH AN IMPROVED FEELING ON THE SKIN BASED ON MIXED GUERBET ALCOHOLS

BACKGROUND OF THE INVENTION

1. Field of the Invention

This invention relates to new cosmetic and/or pharmaceutical formulations which contain as oils Guerbet alcohols based on short-chain fatty alcohol mixtures or esters thereof with selected fatty acids.

2. Discussion of Related Art

The production of cosmetic or pharmaceutical formulations, for example creams, lotions or emollients, involves the use of oil-soluble bases of which the function is to transport polar ingredients, for example active substances or moisture, through the lipid barriers of the skin. Various natural and synthetic oils, for example almond oil or avocado oil or ester oils based on short-chain triglycerides, are suitable for this purpose. The oil components in the formulations in question also perform a skin-care function which is directly related to oiling of the skin. There is a demand among consumers for products which impart a non-tacky, almost instantaneous and relatively long-lasting feeling of smoothness and suppleness to the skin.

The subjective feeling on the skin can be correlated and objectified with the physicochemical parameters of the spreading of the oils on the skin, as illustrated by U. Zeidler in Fette, Seifen, Anstrichmitt. 87, 403 (1985). According to this reference, cosmetic oils can be classified as low-spreading (below 300 $mm^2/10$ mins.), medium-spreading (around 300 to 1000 $mm^2/10$ mins.) and high-spreading oils (above 1000 $mm^2/10$ mins.).

If a high-spreading oil is used as the oil component in a predetermined formulation, the required feeling of smoothness of the skin is achieved very quickly, although the experience does not last long. Conversely, if low-spreading oils are used, the feeling of smoothness is by no means pronounced and remains largely unchanged over a relatively long period so that it is also unsatisfactory. The logical combination of a low-spreading oil with a high-spreading oil surprisingly does not lead to the required additive effect, instead first the strong smoothing effect of the fast-spreading oil component and then, quite independently, the effect of the slow-spreading oil are subjectively perceived. In practice, therefore, it is normally necessary to use complex mixtures of oils adapted exactly to one another which successively develop their respective effects on the lines of a cascade without adversely affecting one another. It is obvious that the development of systems such as these involves considerable outlay on equipment and is therefore in need of improvement from the economic point of view as well [cf. A. Ansmann, SOFW-Journal, 120, 158 (1994)].

Accordingly, the problem addressed by the present invention was to provide new cosmetic and/or pharmaceutical formulations which would be free from the disadvantages mentioned above.

DESCRIPTION OF THE INVENTION

The present invention relates to cosmetic and/or pharmaceutical formulations with an improved feeling on the skin which are characterized in that they contain Guerbet alcohols based on fatty alcohol mixtures containing 6 to 12 carbon atoms and/or esters thereof with fatty acids containing 6 to 22 carbon atoms, the total spreading of the oil components according to Zeidler being in the range from about 300 to 1000 $mm^2/10$ mins.

It has surprisingly been found that cosmetic or pharmaceutical formulations which contain Guerbet alcohols based on fatty alcohol mixtures with the chain length mentioned and/or esters thereof as oils impart the required instantaneous and relatively long-lasting feeling of smoothness to the skin. If, by contrast, Guerbet alcohols based on the pure fatty alcohols are used instead of these Guerbet alcohols or if the Guerbet alcohols based on the pure fatty alcohols are correspondingly mixed, a significantly poorer feeling of the skin is achieved.

In the Guerbetization of alcohol mixtures, mixed Guerbet alcohols are also inevitably formed. Mixed compounds such as these are neither present in Guerbet alcohols obtained by Guerbetization of the pure fatty alcohols nor are they obtainable by mixing Guerbet alcohols based on pure fatty alcohols. However, the invention includes the observation that it is precisely the presence of these mixed compounds—obtained solely by Guerbetization of fatty alcohol mixtures—which is responsible for the surprising skin-care properties of the oils.

The invention also includes the observation that the required effect of smoothness of the skin can be further improved if the Guerbet alcohols mentioned are mixed with other oils, preferably esters of fatty acids with 2-ethyl hexanol, in such a way that the spreading of the oil mixture corresponds to that of a medium-spreading oil and, according to Zeidler, has a value in the range from 350 to 900 $mm^2/10$ mins. It is pointed out even at this juncture that the use of a medium-spreading oil or the use of an oil mixture of which the spreading corresponds to that of a medium-spreading oil also does not lead readily to the required feeling of smoothness of the skin without the addition of the Guerbet alcohols based on fatty alcohol mixtures.

Guerbet alcohols

Guerbet alcohols are known oils which are normally obtained by base-catalyzed condensation of fatty alcohols. An overview of this subject was published by A. J. O'Lennick and R. E. Bilbo in Soap Cosm. Chem. Spec. April, 52 (1987).

Oils suitable for the purposes of the invention are Guerbet alcohols based on fatty alcohols containing 6 to 12 and preferably 8 to 10 carbon atoms. Typical examples are Guerbet alcohols based on mixtures containing caproic alcohol, caprylic alcohol, capric alcohol and/or lauryl alcohol. A typical fatty alcohol mixture within the C chain length range mentioned is the so-called $C_{8/10}$ head-fractionated fatty alcohol which is obtained as a cut in the distillation of, for example, coconut oil, palm oil or palm kernel oil. A Guerbet alcohol based on a fatty alcohol with a C chain distribution of <5% by weight $C_6$, 50 to 60% by weight $C_8$, around 35 to 45% by weight $C_{10}$ and <2% by weight $C_{12}$ is particularly preferred.

Guerbet esters

The Guerbet alcohols mentioned above may also be used in the form of their esters with fatty acids containing 6 to 22 carbon atoms, preferably 8 to 18 carbon atoms and more preferably 12 to 14 carbon atoms. Typical examples are esters of Guerbet alcohols with caproic acid, caprylic acid, 2-ethylhexyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids.

The Guerbet esters may have a degree of esterification of 100%, although partial esters with a degree of esterification of 20 to 90% and, more particularly, 40 to 70% of the theoretical are preferably used. Esters based on the above-mentioned Guerbet alcohols with technical $C_{8-18}$ or $C_{12-14}$ cocofatty acids which have a degree of esterification of 40 to 70 are particularly preferred. Corresponding mixtures of completely esterified Guerbet esters and the corresponding Guerbet alcohols in a ratio by weight of 10:90 to 90:10 and preferably 30:70 to 70:30 are equally suitable.

Oils

The formulations according to the invention may contain other oils of which the choice is not critical as long as the mixture of the oils with the Guerbet alcohols based on short-chain fatty alcohol mixtures has a Zeidler spreading value comparable with that of a medium-spreading oil, i.e. in the range from about 300 to 1000 mm$^2$/10 mins. Examples of oils which may be used in the formulations in addition to the Guerbet alcohols mentioned are:

b1) esters of linear $C_{6-20}$ fatty acids with linear $C_{6-20}$ fatty alcohols,
b2) esters of branched $C_{6-13}$ carboxylic acids with linear $C_{6-18}$ fatty alcohols,
b3) esters of linear $C_{10-18}$ fatty acids with branched alcohols, more especially 2-ethyl hexanol,
b4) esters of linear and/or branched fatty acids with dihydric alcohols,
b5) triglycerides based on $C_{6-10}$ fatty acids,
b6) vegetable oils,
b7) branched primary alcohols,
b8) substituted cyclohexanes and/or
b9) dialkyl ethers.

Typical examples are esters of capric acid and caprylic acid with cocofatty alcohols, esters of coconut oil or palm kernel oil fatty acid with 2-ethyl hexanol, oleic acid decyl ester, isononanoic acid cetearyl ester, triglycerides based on capric/caprylic acid, isocetyl alcohol, di-n-octyl cyclohexane, di-i-octyl cyclohexane, di-n-octyl ether and di-2-ethylhexyl ether.

A combination of the Guerbet alcohols mentioned with fatty acid-2-ethylhexyl esters has also proved to be extremely advantageous. From the sensorial point of view, it is of particular advantage to use a mixture of a Guerbet alcohol based on a mixture of fatty alcohols containing 6 to 12 carbon atoms and a 2-ethylhexyl ester based on a fatty acid with the following C chain distribution: <3% by weight $C_{14}$, 45 to 53% by weight $C_{16}$, 43 to 52% by weight $C_{18}$ and <2% by weight $C_{18}$.

Composition of the formulations

The cosmetic and/or pharmaceutical formulations according to the invention may contain a) the Guerbet alcohols and/or Guerbet esters and b) other oils which meet the spreading range requirement in a ratio by weight of 100:0 to 10:90, preferably in a ratio by weight of 90:10 to 10:90 and more preferably in a ratio by weight of 70:30 to 30:70. The formulations may be produced by methods known per se, for example by hot, cold, hot-hot/cold or PIT emulsification. These are purely mechanical processes which do not involve a chemical reaction.

Examples of mixtures of the type mentioned are mixtures of a Guerbet alcohol based on a $C_{6-12}$ fatty alcohol mixture with $C_{16/18}$ fatty acid-2-ethylhexyl ester, oleic acid decyl ester, oleic acid oleyl ester, triglycerides based on $C_{8/10}$ fatty acid or isononanoic acid cetearyl ester in a ratio by weight of 50:50. Further examples are mixtures of a Guerbet alcohol based on a $C_{6-12}$ fatty alcohol mixture with almond oil in a ratio by weight of 90:10 or with di-n-octyl ether in a ratio by weight of 80:20.

In addition, the formulations, for example creams and lotions, may contain emulsifiers, fats and waxes, stabilizers and superfatting agents, thickeners, biogenic acids, film formers, preservatives, dyes and fragrances.

Suitable emulsifiers are both known w/o and also o/w emulsifiers such as, for example, hydrogenated and ethoxylated castor oil, polyglycerol fatty acid esters or polyglycerol polyricinoleates or polyglycerol poly-12-hydroxystearates.

Typical examples of fats are glycerides while suitable waxes are inter alia beeswax, paraffin wax or microwaxes, optionally in combination with hydrophilic waxes, for example cetostearyl alcohol.

Suitable stabilizers are metal salts of fatty acids, for example magnesium, aluminium and/or zinc stearate.

Suitable superfatting agents are such substances as, for example, polyethoxylated lanolin derivatives, lecithin derivatives, polyol fatty acid esters, monoglycerides and fatty acid alkanolamides, the fatty acid alkanolamides also serving as foam stabilizers.

Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone; surfactants such as, for example, narrow-range fatty alcohol ethoxylates or alkyl oligoglucosides and also electrolytes, such as sodium chloride and ammonium chloride.

Biogenic acids in the context of the invention are, for example, plant extracts and vitamin complexes.

Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives and similar compounds.

Suitable preservatives are, for example, phenoxyethanol, formaldehyde solution, parabens, pentanediol or sorbic acid.

Suitable pearlescers are, for example, glycol distearic acid esters, such as ethylene glycol distearate, and also fatty acid monoglycol esters and fatty acids.

Suitable dyes are the substances suitable and permitted for cosmetic purposes as listed, for example, in the publication "Kosmetische Färbemittel" of the Farbstoffkommission der Deutschen Forschungsgemeinschaft, published by Verlag Chemie, Weinheim, 1984, pages 81 to 106. These dyes are normally used in concentrations of 0.001 to 0.1% by weight, based on the mixture as a whole.

The total content of auxiliaries and additives may be from 1 to 50% by weight and is preferably from 5 to 40% by weight while the non-aqueous component ("active-substance content") makes up from 20 to 80% by weight and preferably from 30 to 70% by weight of the formulations.

Commercial Applications

The cosmetic and/or pharmaceutical formulations according to the invention may be o/w and/or w/o emulsions, multiple w/o/w emulsions and purely lipophilic oils or gels. They have fatting properties and impart a rapid, long-lasting and uniformly diminishing feeling of smoothness to the skin. The problem of the "smoothing gap" is reliably avoided. The Guerbet alcohols based on short-chain fatty alcohol mixtures and/or the corresponding esters may be present in the formulations in quantities of 1 to 99% by weight and are preferably present in the emulsions in quantities of 5 to 30% by weight, based on the formulations.

The following Examples are intended to illustrate the invention without limiting it in any way.

EXAMPLES

I. Zeidler spreading values

The spreading values of various oils were determined by the Zeidler method. To this end, quantities of 4 mg of the oil component were applied to the inside of the lower arm of a test subject which had been rubbed beforehand with cotton wool moistened with ethanol. The test was conducted in an atmosphere of 23° C./60% relative air humidity. After 10 minutes, an impression of the spread lipid was taken with tracing paper and the surface area determined (cf. Table 1).

TABLE 1

Spreading (S) of oils [mm²/10 mins]

| Ex. | Oil | S |
|---|---|---|
| B1 | Almond oil | 200 |
| B2 | $C_{16/18}$ fatty acid-2-ethylhexyl ester | 800 |
| B3 | Guerbet alcohol based on caprylic alcohol [Eutanol ® G 16] | 700 |
| B4 | Guerbet alcohol based on caprylic alcohol | 600 |
| B5 | Oleic acid decyl ester [Cetiol ® V] | 700 |
| A1 | Guerbet alcohol based on $C_{6/10}$ fatty alcohol | 650 |
| A2 | Guerbet alcohol based on $C_{6/10}$ fatty alcohol/ $C_{12/14}$ cocofatty acid ester | 730 |
| B6 | Triglyceride based on $C_{8/10}$ fatty acid [Myritol ® 318] | 550 |
| B7 | Isononanoic acid cetearyl ester [Cetiol ® SN] | 700 |
| B8 | Di-n-octyl ether [Cetiol ® OE] | 1600 |

II. Subjective evaluation by a test panel

A panel consisting of 5 experienced examiners tested formulations based on a standard skin cream containing various oil mixtures for their subjective feeling of smoothing of the skin. Evaluation was based on a scale of 1 (hardly any smoothing or rapid disappearance of the feeling of smoothness) to 6 (rapid uniform feeling of smoothness).

The figures in Table 2 are average values. Examples 1 to 11 correspond to the invention while Examples C1 to C9 are intended for comparison.

TABLE 2

Subjective feeling of smoothness of the skin

| Ex. | Component 1 | Component 2 | Ratio | Smoothness of the skin |
|---|---|---|---|---|
| 1 | A1 | — | 100:0 | 5.1 |
| 2 | A1 | B1 | 90:10 | 5.2 |
| 3 | A1 | B2 | 50:50 | 5.8 |
| 4 | A1 | B5 | 50:50 | 5.7 |
| 5 | A1 | B6 | 50:50 | 5.2 |
| 6 | A1 | B7 | 50:50 | 5.2 |
| 7 | A1 | B8 | 80:20 | 5.4 |
| 8 | A2 | — | 100:0 | 5.1 |
| 9 | A1 | A2 | 50:50 | 5.8 |
| 10 | A1 | A2 | 70:30 | 5.6 |
| 11 | A1 | A2 | 30:70 | 5.4 |
| C1 | — | B1 | 0:100 | 1.5 |
| C2 | — | B2 | 0:100 | 3.5 |
| C3 | — | B3 | 0:100 | 3.0 |
| C4 | — | B4 | 0:100 | 3.0 |
| C5 | B3 | B4 | 50:50 | 3.0 |
| C6 | — | B5 | 0:100 | 3.0 |
| C7 | — | B6 | 0:100 | 3.0 |
| C8 | — | B7 | 0:100 | 3.0 |
| C9 | — | B8 | 0:100 | 2.0 |

Above an average value of 5.0, the feeling of smoothing of the skin is excellent; below 5.0, the result is unsatisfactory. The results show that a satisfactory result is only obtained with Guerbet alcohols based on short-chain fatty alcohol mixtures or esters thereof or with mixtures of these Guerbet alcohols with other oil components within the claimed spreading range.

What is claimed is:

1. A cosmetic or pharmaceutical composition having an improved feel on the skin, said composition containing as oil components Guerbet alcohols prepared from mixtures of fatty alcohols having differing chain lengths and containing 6 to 12 carbon atoms or esters thereof with fatty acids containing 6 to 22 carbon atoms, wherein the spreading value of the oil components as determined by the Zeidler method is from about 300 to about 1,000 mm²/10 minutes.

2. A composition as in claim 1 containing partial esters of Guerbet alcohols prepared from fatty alcohol mixtures containing 6 to 12 carbon atoms with fatty acids containing 12 to 14 carbon atoms, and wherein the degree of esterification of said partial esters is from 20% to 90%.

3. A composition as in claim 1 containing fatty acid esters of 2-ethyl hexanol.

* * * * *